United States Patent [19]

Okuda et al.

[11] Patent Number: 5,440,402
[45] Date of Patent: Aug. 8, 1995

[54] METHOD AND APPARATUS FOR RECOGNIZING PASTER PORTION OF WEB

[75] Inventors: Tetsuya Okuda; Shinichi Kojima, both of Ibaraki, Japan

[73] Assignee: Komori Corporation, Tokyo, Japan

[21] Appl. No.: 965,752

[22] Filed: Oct. 23, 1992

[30] Foreign Application Priority Data

Oct. 31, 1991 [JP] Japan .................. 3-311408

[51] Int. Cl.⁶ ............... B41F 33/18; B65H 26/02
[52] U.S. Cl. ..................... 358/406; 346/24; 346/28; 346/136; 178/42; 358/492; 358/498
[58] Field of Search ........... 358/406, 488, 489, 490, 358/492, 498; 178/23 R, 42; 346/24, 28, 33 R, 134, 136, 138, 146

[56] References Cited

U.S. PATENT DOCUMENTS 3,975,590 8/1976 Nelson .
4,054,884 10/1977 Nelson .

FOREIGN PATENT DOCUMENTS 0437648 7/1991 European Pat. Off. .
4124397 4/1992 Germany .
2066949 7/1981 United Kingdom .

OTHER PUBLICATIONS

Patent Abstracts of Japan, vol. 12, No. 394 (P-773)(3241) Oct. 20, 1988 & JP-A-63 134 938 (Canon).

*Primary Examiner*—Bentsu Ro
*Attorney, Agent, or Firm*—Blakely, Sokoloff, Taylor & Zafman

[57] ABSTRACT

According to a method and apparatus for recognizing a paster portion of a web, each pixel data of a printed matter serving as a reference is stored as reference image data. Each pixel data of a printed matter serving as a test target printed on the web is stored as test image data. The reference image data is compared with the test image data in units of pixels to detect defective pixels. The paster portion of the web is recognized on the basis of a generation pattern of the defective pixels.

14 Claims, 6 Drawing Sheets

METHOD AND APPARATUS FOR RECOGNIZING PASTER PORTION OF WEB

BACKGROUND OF THE INVENTION

The present invention relates to a method and apparatus for recognizing a paster portion of a web in a rotary press, in which a bonded portion (i.e., a paster portion) between new and old webs is recognized to detect predetermined areas in the downstream and upstream of this paster portion as printing defects, thereby automatically eliminating the predetermined areas.

Figure 6:
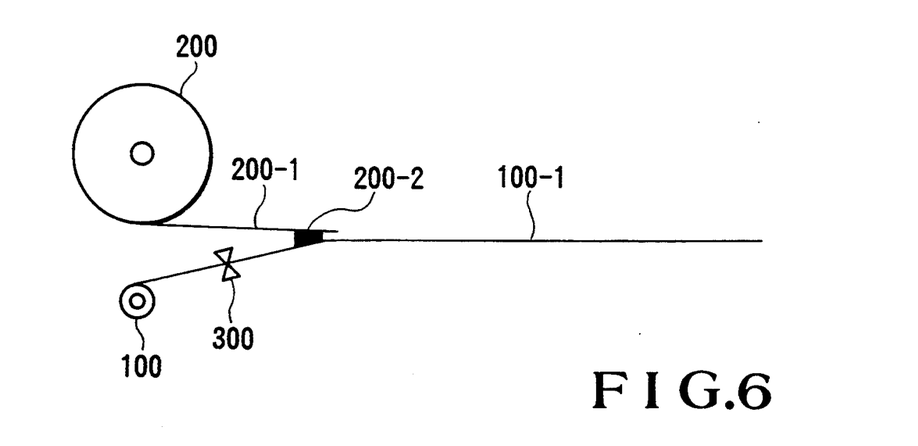
FIG. 6 is a side view of the main part showing a paper pasting condition in a rotary press.

FIG. 6 shows a paper pasting condition in a rotary press. Referring to FIG. 6, reference numeral 100 denotes an old roll; 200, a new roll; 100-1, an old web supplied from the old roll 100 to a printing unit; and 200-1, a new web to be supplied from the new roll 200.

A double-coated tape 200-2 is adhered to the leading web end of the new roll 200 such that the adhesive surface of the tape 200 is exposed. During feeding of the old web 100-1, when the diameter of the old roll 100 reaches the minimum diameter, the old web 100-1 is bonded to the new web 200-1 through the double-bonded tape 200-2 at a predetermined timing, and a knife mechanism 300 is actuated to cut the old web 100-1.

Figure 7A:
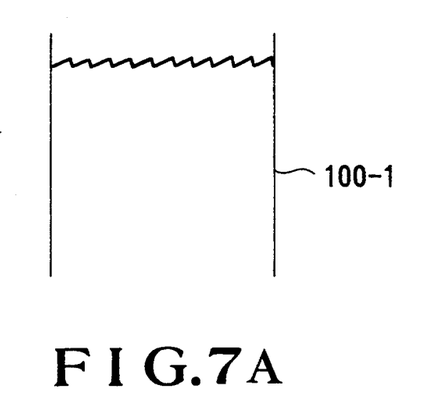
FIGS. 7A and 7B are views showing an example of the cut shape of an old web and the leading web end of a new web at a paster portion.
Figure 7B:
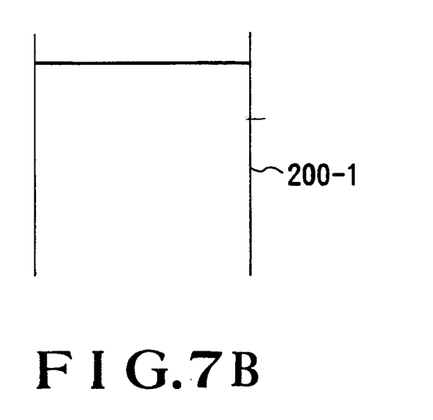
Figure 8A:
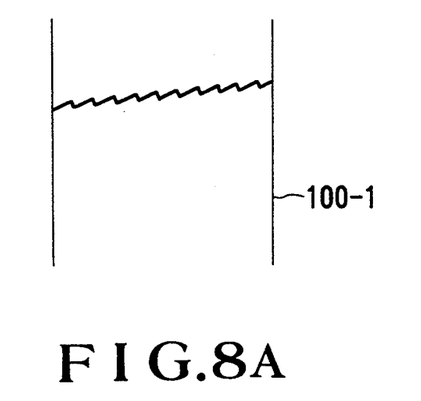
FIGS. 8A and 8B are views showing another example of the cut shape of an old web and the leading web end of a new web at a paster portion.
Figure 8B:
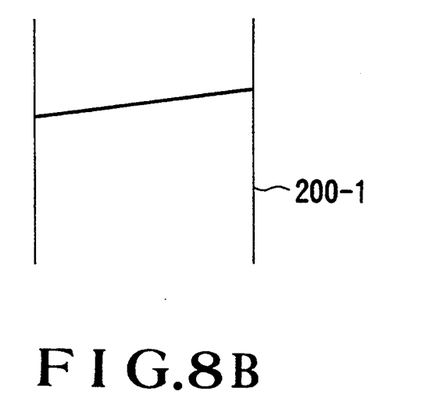

The end of the old web 100-1 cut by the knife mechanism 300 has a saw-toothed wave shape, as shown in FIG. 7A. The leading web end face of the new web 200-1 is straight, as shown in FIG. 7B. The old web 100-1 and the new web 200-1 may be bonded obliquely, as shown in FIGS. 8A and 8B, depending on the paper pasting condition.

When the old web 100-1 and the new web 200-1 are bonded as described above, a printing defect is formed due to the influence of a tension varying at the time of bonding.

For this reason, a bonded portion (to be referred to as a paster portion hereinafter) between the old web 100-1 and the new web 200-1 is found in the subsequent process, and start and end positions of the upstream and downstream printing defects of the paster portion as the boundary are found, thereby eliminating the found printing defects.

In the prior art, however, since the search and elimination of the printing defects with respect to the paster portion as the boundary are manually performed, they are time-consuming and cumbersome, thus overloading the operator.

SUMMARY OF THE INVENTION

It is an object of the present invention to provide a method and apparatus for recognizing a paster portion of a web, wherein the paster portion of the web can be automatically recognized.

It is another object of the present invention to provide a method and apparatus for recognizing a paster portion of a web, wherein the paster portion of the web can be automatically eliminated.

It is still another object of the present invention to provide a method and apparatus for recognizing a paster portion of a web, wherein the load on the operator for searching and eliminating the paster portion can be reduced.

In order to achieve the above objects according to an aspect of the present invention, there is provided a method of recognizing a paster portion of a web, comprising the steps of storing, as reference image data, each pixel data of a printed matter serving as a reference, inputting, as test image data, each pixel data of a printed matter serving as a test target printed on the web, comparing the reference image data with the test image data in units of pixels to detect defective pixels, and recognizing the paster portion of the web on the basis of a generation pattern of the defective pixels.

In order to achieve the above objects according to another aspect of the present invention, there is provided an apparatus for recognizing a paster portion of a web, comprising reference data storage means for storing, as reference image data, each pixel data of a printed matter serving as a reference, test data inputting means for inputting, as test image data, each pixel data of a printed matter serving as a test target printed on the web, defective pixel detecting means for comparing the reference image data with the test image data in units of pixels to detect defective pixels, and paster portion recognizing means for recognizing the paster portion of the web on the basis of a generation pattern of the defective pixels.

DETAILED DESCRIPTION OF THE PREFERRED EMBODIMENT

A preferred embodiment of the present invention will be described in detail with reference to the accompanying drawings.

Figure 1:
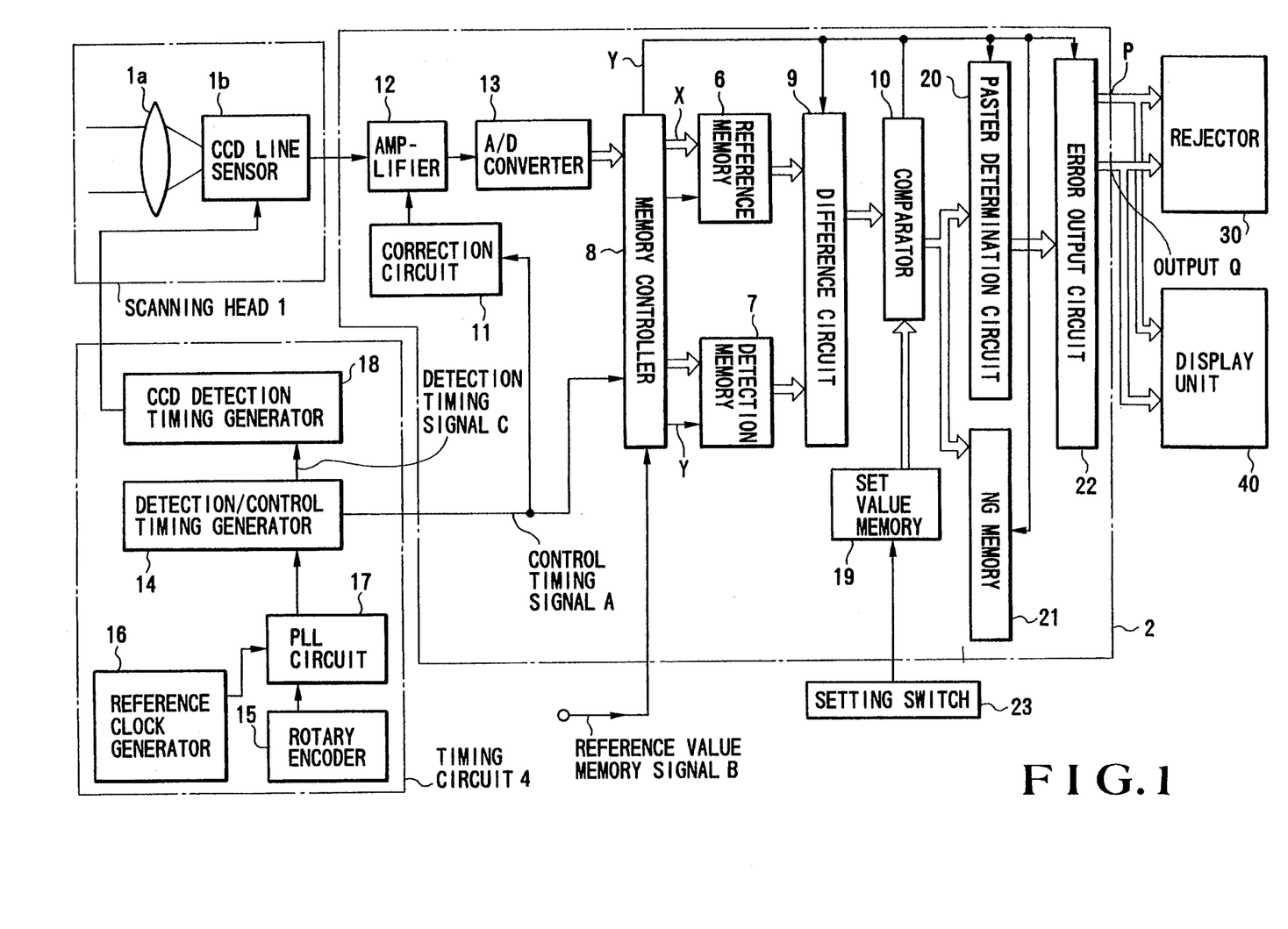
FIG. 1 is a block diagram of a paster portion recognizing apparatus according to an embodiment of the present invention.

FIG. 1 shows a web paster portion recognizing apparatus for a printing press according to an embodiment of the present invention. A scanning head 1 serving as an image pickup means comprises an optical system such as a lens 1a and a CCD line sensor 1b for converting an image focused through the optical system into an electrical signal. The scanning head 1 can pick up the resultant printed matter as an image.

A signal processor 2 comprises a reference memory 6 for storing input reference image data, a detection memory 7 for storing input test image data, a memory controller 8 for controlling read access and write access of the reference memory 6 and the detection memory 7, a difference circuit 9 for calculating a difference between pixel data read out from the reference memory 6 and the detection memory 7, a comparator 10 for comparing an output from the difference circuit 9 with a set value, a correction circuit 11 for correcting the output level of an amplifier, an amplifier 12 for amplifying an output from the CCD line sensor 1b in the scanning head 1, an A/D converter 13 for receiving an output from the amplifier 12 and outputting digital data to the memory controller 8 upon A/D conversion, a set value memory 19 for outputting a value set by a setting switch 20 to the comparator 10, a paster determination circuit 20 for receiving an output from the comparator 10 to determine the presence/absence of a paster, an NG memory 21 for storing pixel position data from the difference circuit 9 in accordance with an output from the paster determination circuit 20, and an error output circuit 22 for performing two types of error outputs on the basis of the output from the paster determination circuit 20. Reference numeral 30 denotes a rejector for receiving an error output from the error output circuit 22 to reject the printed matter. Reference numeral 40 denotes a display unit for displaying a web position and performing an alarm display. Reference symbol X denotes pixel data; and Y, a step signal representing a pixel address or the like.

The signal processor 2 is controlled by an external control timing signal A and a reference value memory signal B. More specifically, the control timing signal A comprises a reference signal as a pulse signal rising every rotation of a plate cylinder in a printing press (not shown) and a clock pulse as a read/write pulse signal rising every rotation of the plate cylinder. The control timing signal A is output from a detection/control timing generator 14 and is supplied to the memory controller 8 and the correction circuit 11 in the signal processor 2. On the other hand, the reference value memory signal B is supplied upon a turn-on operation of a switch (not shown) or supplied from a tone change recognition circuit 3 (to be described above) to the memory controller 8 in the signal processor 2.

The detection/control timing generator 14 comprises an up/down counter. The intervals of a detection timing signal C and the control timing signal A as output signals from the detection/control timing generator 14 are changed in accordance with a printing press speed detected by a rotary encoder 15 serving as a rotation detecting means. A PLL circuit 17 compares a reference clock pulse output from a reference clock generator 16 with the pulse signal representing the speed output from the rotary encoder 15 to control the detection/control timing generator 14 so as to output the detection timing signal C and the control timing signal A, both of which correspond to the printing press speed. Reference numeral 18 denotes a CCD detection timing generator for controlling the CCD line sensor 1b every rotation of the plate cylinder upon reception of the detection timing signal C so as to cause the signal processor 2 to receive a video signal. The detection/control timing generator 14, the rotary encoder 15, the reference clock generator 16, the PLL circuit 17, and the CCD detection timing generator 18 constitutes a timing circuit 4.

In this embodiment, read access of the video signal from the CCD line sensor 1b and signal processing timings in the signal processor 2 are changed so as to follow the printing press speed (rotational speed of the plate cylinder) detected by the rotary encoder 15.

The operation of the web paster portion recognizing apparatus having the above arrangement will be described below.

At the start of printing, states of actual printed matters are visually checked while test printing is being performed. If the printed matters are determined to be satisfactory, a switch (not shown) is turned on to output the reference value memory signal B. Thereafter, when the detection timing signal C and the control timing signal A which represent a reference position are output from the detection/control timing generator 14, the CCD line sensor 1b is driven in accordance with an output from the CCD detection timing generator 18, thereby performing read access of the reference memory 6 for the reference image data from the printed matter serving as the reference. This read access is performed in accordance with the control timing signal A output from the detection/control timing generator 14 controlled by a clock pulse from the rotary encoder 15.

The reference image data read from the CCD line sensor 1b is stored in the reference memory 6 through the amplifier 12, the A/D converter 13, and the memory controller 8. After the reference image data is stored in the reference memory 6, test image data of the printed matter serving as a detection object is read during rotation of the plate cylinder upon progress of the printed matter. The read test image data is stored in the detection memory 7 selected by the memory controller 8.

The difference circuit 9 calculates a level difference between the corresponding pixel data of the reference image data output from the reference memory 6 and the test image data output from the detection memory 7. Data representing the level difference is output to the comparator 10. The comparator 10 compares the level difference input from the difference circuit 9 with a predetermined value stored in the set value memory 19. If the level difference is larger than the predetermined value, the comparator 10 outputs a comparison output representing a printing defect to the paster determination circuit 20.

Figure 3:
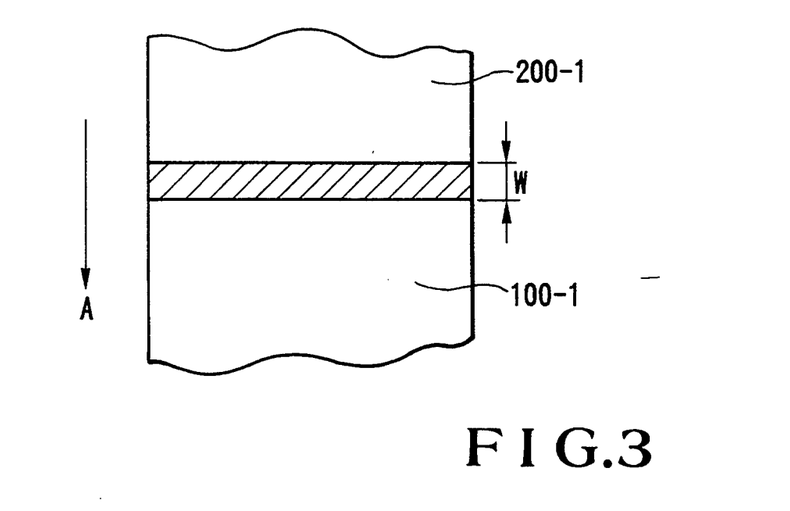
FIG. 3 is a view for explaining the basic operation of a paster determination circuit in the paster portion recognizing apparatus.

The paster determination circuit 20 detects a defective pixel position every lateral pixel line when a printing direction A is defined as the longitudinal direction of the web. The defective pixels are logically ORed every longitudinal pixel line of an area constituted by a predetermined line width (line count) W in which defective pixels are continuously detected. If the sum of OR products, i.e., the total number of longitudinal pixel lines in which defective pixels are detected, exceeds a preset value, the paster determination circuit 20 determines that the paster portion between the old web 100-1 and the new web 200-1 is located within the predetermined line width W. The sum of OR products can approximate the frequency of occurrence of defective pixels in the lateral direction within the predetermined line width.

More specifically, a linear pasting line is formed laterally in the paster portion between the old web 100-1 and the new web 200-1. This pasting line may be slightly inclined depending on a paper pasting condition. Pixels through which this pasting line passes are determined as the printing defects. That is, a large number of defective pixels are formed laterally within the predetermined line width W, this is detected as the pasting line, i.e., the paster portion between the old web 100-1 and the new web 200-1. The large number of defective pixels in the lateral direction can be detected such that defective pixels present at random in the respective longitudinal pixel lines within the predetermined line width W are checked in units of longitudinal pixel lines and the checked defective pixels are added in the lateral direction.

Figure 4:
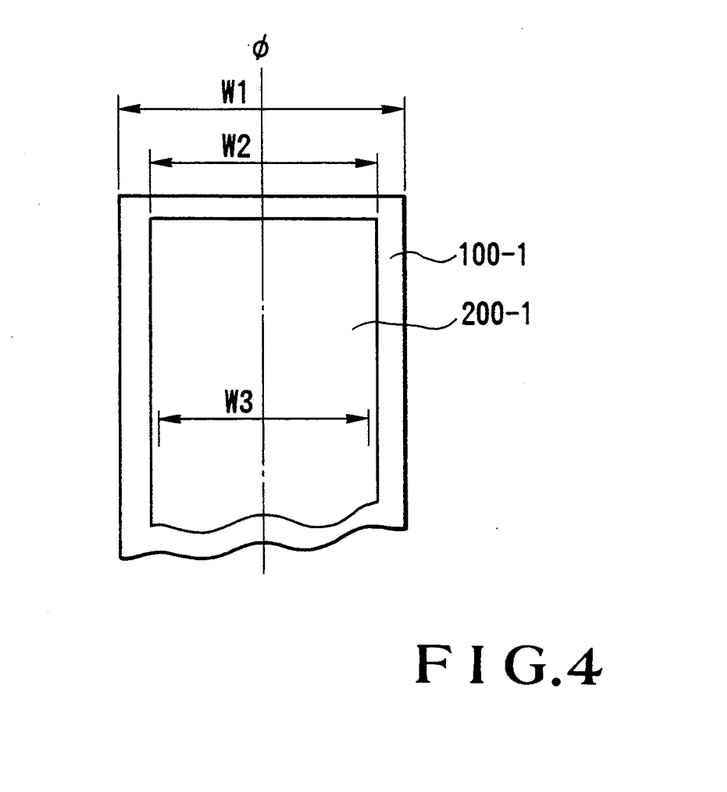
FIG. 4 is a view showing a width W3 of one lateral pixel line to determine a paster portion in the paster portion recognizing apparatus of the present invention.

The function of the paster determination circuit 20 will be described in detail. The paster determination circuit 20 performs paster determination on the basis of a web having a smaller paper width if the old and new webs 100-1 and 200-1 have different widths. For example, as shown in FIG. 4, when a paper width W2 of the new web 200-1 is smaller than a paper width W1 of the old web 100-1, a width W3 slightly smaller than the paper width W2 is defined as the width of one lateral pixel line in determination of the paster portion. The center $\phi$ of the old web 100-1 during printing is the same as that of the new web 200-1 during printing. This determination is performed on the basis of pixel addresses in one lateral pixel line from the memory controller 8.

Figure 5:
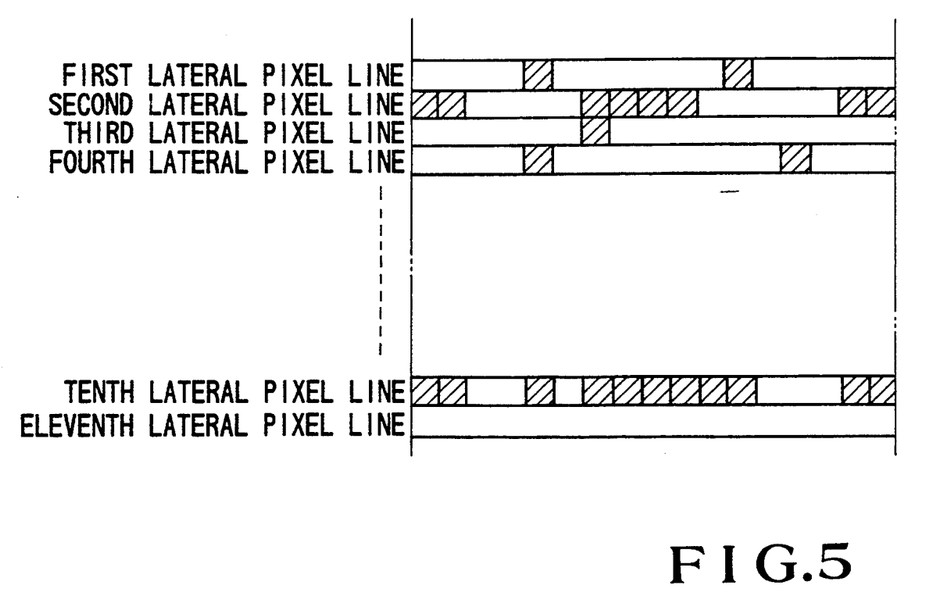
FIG. 5 is a view conceptually illustrating the storage contents of an NG memory in the paster portion recognizing apparatus according to the present invention.

The paster determination circuit 20 monitors the defective pixels every lateral pixel line having the width W3. If a defective pixel is detected, its position is stored in the NG memory 21. If the predetermined line width W represents 10 lines, one lateral pixel line from which the first defective pixel is detected is defined as the first line, and positions of defective pixels of all lines up to the eleventh line are stored in the NG memory 21. FIG. 5 conceptually illustrates the storage contents of the NG memory 21. The defective pixels are represented by cross-hatched lines in FIG. 5.

The paster determination circuit 20 logically ORs the defective pixels of every longitudinal pixel line constituted by the first to tenth lateral pixel lines on the basis of the storage contents of the NG memory 21. The first condition is defined such that the sum of longitudinal pixel lines having defective pixels represented as the sum of OR products, i.e., the sum of defective pixels in the logically ORed lateral pixel lines constituted by the respective OR products on the arithmetic basis, is a set value or more. The second condition is defined as the end of longitudinal pixel lines containing defective pixels continuous within the predetermined line width. When the first and second conditions are satisfied, the paster determination circuit 20 determines that the paster portion is located in the area constituted by these longitudinal pixel lines. That is, in the above case, after the longitudinal pixel lines which do not contain defective pixels are confirmed up to the eleventh line, the paster determination circuit 20 determines that the paster portion between the old and new webs 100-1 and 200-1 is located within the lines from the first to tenth lines.

On the other hand, when the first and second conditions are not satisfied, the paster determination circuit 20 determines a normal printing defect. For example, when longitudinal pixel lines containing continuous defective pixels continue by the predetermined line width W or more, the line width at which defective pixels are detected is excessively large. The paster determination circuit 20 does not determine that defective pixels are detected by a paster portion. According to the present invention, defective pixels are detected at a predetermined frequency of occurrence or more only within the predetermined line width, and then a paster portion is recognized.

The determination result of the paster determination circuit 20 is sent to the error output circuit 22. When it is determined that the paster portion between the old web 100-1 and the new web 200-1 is located between the first and tenth lines, the error output circuit 22 outputs a paster portion elimination signal P to the rejector 30. The paster portion elimination signal P is output when the paster portion reaches near the rejector 30. 10 downstream and 30 upstream pages of the printed matter with respect to the paster portion as the boundary are eliminated as the printing defects.

On the other hand, when the determination result represents a normal printing defect, the error output circuit 22 outputs a printing defect elimination signal Q. This printing defect elimination signal Q is output when the printing defect reaches near the rejector 30. Therefore, a few downstream pages and a few upstream pages of the printed matter including this printing defect are eliminated as the printing defects.

The output from the error output circuit 22 is sent to the display unit 40 to display a paster position or a printing defect position and perform an alarm display.

Figure 2A:
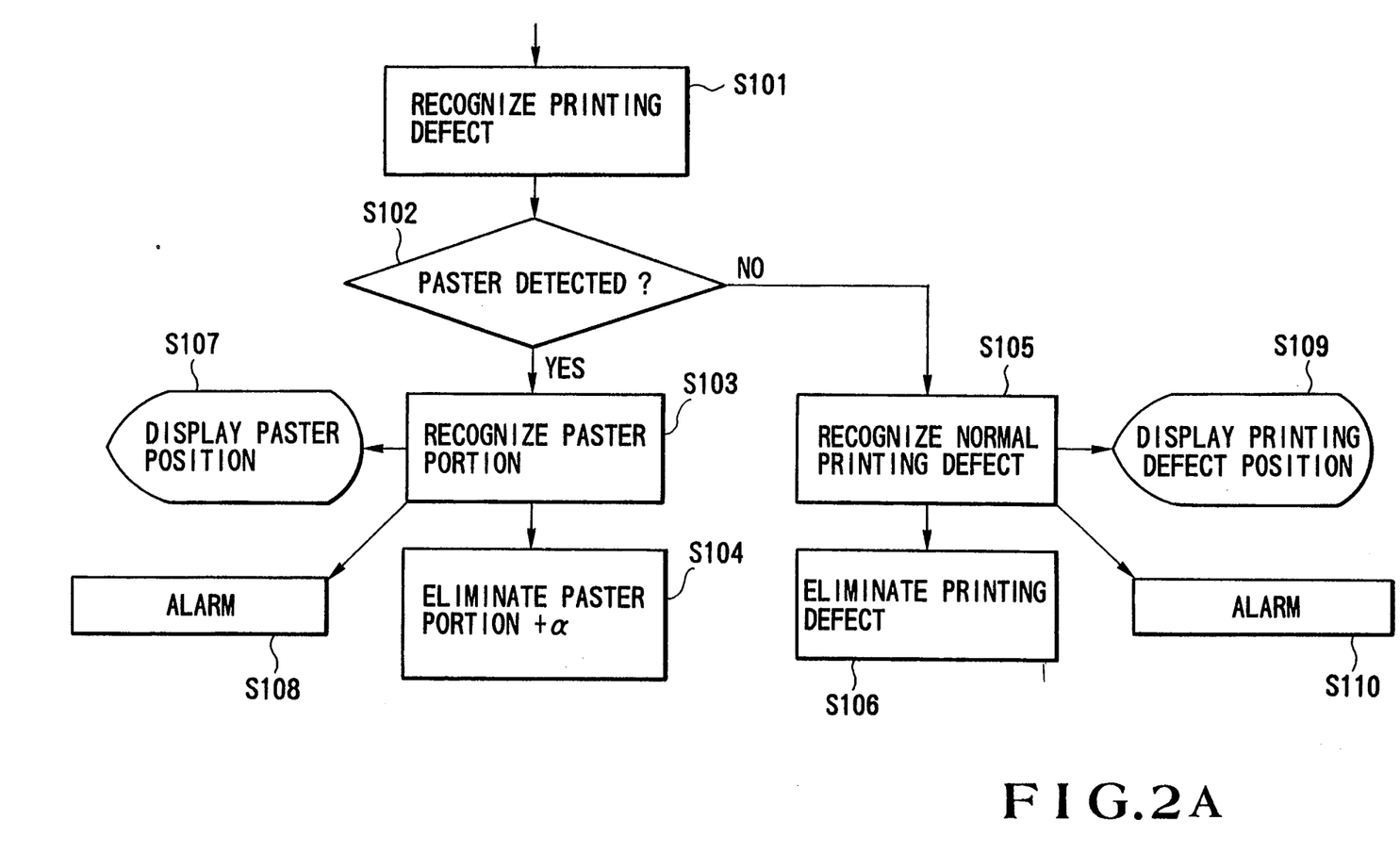
FIGS. 2A and 2B are flow charts showing a paster portion recognizing method according to the embodiment of the present invention.
Figure 2B:
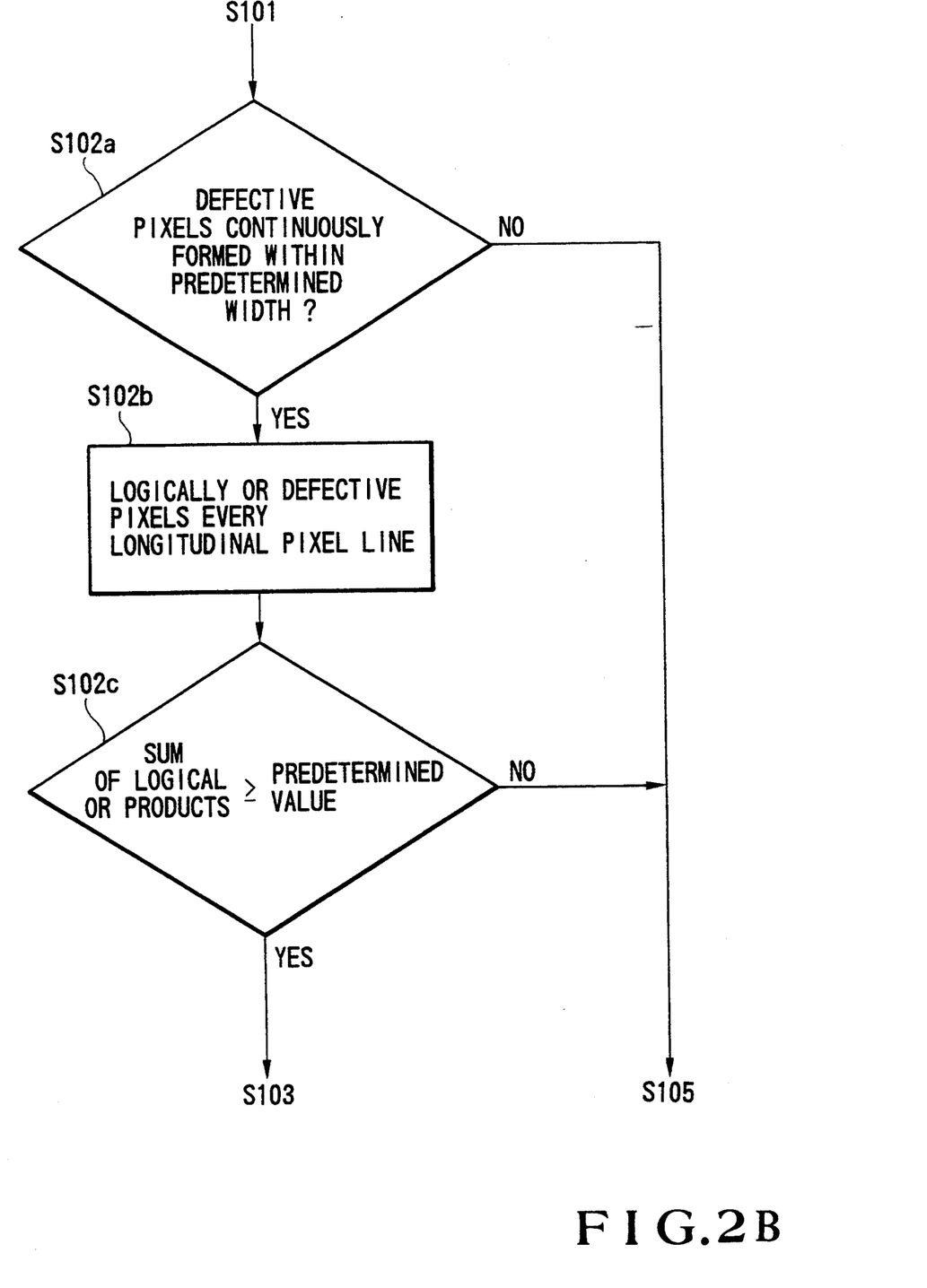

FIGS. 2A and 2B are flow charts showing a paster portion recognizing method according to the present invention. In step S101, when the paster determination circuit 20 recognizes a printing defect in step S101, the circuit 20 determines whether this printing defect is caused by a web paster portion (step S102). If YES in step S102, the paster determination circuit 20 recognizes that the paster portion is located in this printing defect (step S103). 10 downstream and 30 upstream pages of the printed matter including the paster portion are eliminated by the rejector 30 through the error output circuit 22 (step S104). On the other hand, if the paster determination circuit 20 determines in step S102 that the printing defect is not caused by the paster portion, it determines that the printing defect is a normal printing defect (step S105). In this case, a few downstream pages and a few upstream pages of the printed matter containing the printing defect are eliminated as the printing defects by the rejector 30 (step S106).

When the paster portion is recognized in step S103, the position of this paster portion is displayed on the display unit 40 (step S107), and an alarm tone is produced to inform this display operation (step S108). Similarly, when the normal printing defect is recognized, the position of this normal printing defect is displayed on the display unit 40 (step S109), and an alarm tone is produced to inform this display operation (step S110).

Step S102 for detecting the paster portion is shown in FIG. 2B in detail. It is determined in step S102a whether the number of continuous lateral pixel lines containing defective pixels falls within a predetermined line count. If YES in step S102a, the defective pixels are logically ORed every longitudinal pixel contained in the continuous defective pixel portion detected in step S102b. It is determined in step S102c whether the sum of logically ORed defective pixels is a predetermined value or more. If YES in step S102c, the flow advances to step S107 to recognize the paster portion. On the other hand, if NO in steps 102a and 102c, the flow advances to step S105 to recognize that the printing defect is a normal printing defect.

As has been apparent form the above description, according to the present invention, defective pixels having a high density within only a predetermined line width are detected to recognize a paster portion between new and old webs. Upstream and downstream pages of the printed matter with respect to the paster portion as the boundary can be automatically eliminated, thereby greatly reducing the load of the operator.

What is claimed is:

1. A method of recognizing a paster portion of a web, comprising the steps of:
storing, as reference image data, each pixel data of a printed matter serving as a reference;
inputting, as test image data, each pixel data of a printed matter serving as a test target printed on said web;
comparing the reference image data with the test image data in units of pixels to detect defective pixels; and
recognizing said paster portion of said web on the basis of a generation pattern of the defective pixels.

2. A method according to claim 1, wherein the step of inputting the pixel data comprises the step of storing the input test image data, thereby comparing the stored reference image data and the stored test image data.

3. A method according to claim 1, wherein the step of recognizing said paster portion comprises the step of detecting that the defective pixels are continuously formed within a predetermined width in a convey direction of said web and the step of detecting that the defective pixels are formed in an area, where the defective pixels are continuously formed, not less than a predetermined frequency of occurrence in a direction perpendicular to the convey direction of said web.

4. A method according to claim 1, wherein the step of recognizing said paster portion comprises the first step of detecting that lateral pixel lines of said web which contain the defective pixels continue within a predetermined line count, and the second step of detecting that the number of longitudinal pixel lines containing the defective pixels is not less than a predetermined count in an area of the lateral pixel lines in which the defective pixels are continuously formed.

5. A method according to claim 4, wherein the second step comprises the step of logically ORing the defective pixels every longitudinal pixel line and the step of detecting that a sum of defective pixels of the logically ORed lateral pixel lines as a logical OR result is not less than a predetermined value.

6. A method according to claim 1, further comprising the step of eliminating, as printing defects, predetermined downstream and upstream areas with respect to said recognized paster portion as a boundary.

7. A method according to claim 1, further comprising the step of displaying a position of said recognized paster portion and performing an alarm display of generation of said paster portion.

8. An apparatus for recognizing a paster portion of a web, comprising:
reference data storage means for storing, as reference image data, each pixel data of a printed matter serving as a reference;
test data inputting means for inputting, as test image data, each pixel data of a printed matter serving as a test target printed on said web;
defective pixel detecting means for comparing the reference image data with the test image data in units of pixels to detect defective pixels; and
paster portion recognizing means for recognizing said paster portion of said web on the basis of a generation pattern of the defective pixels.

9. An apparatus according to claim 8, wherein said test data inputting means comprises test data storage means for storing the input test image data therein, thereby said defective pixel detecting means comparing the reference image data stored in said reference data storage means and the test image data stored in said test data storage means.

10. An apparatus according to claim 8, wherein said paster portion recognizing means comprises first detecting means for detecting that the defective pixels are continuously formed within a predetermined width in a convey direction of said web and second detecting means for detecting that the defective pixels are formed in an area, where the defective pixels are continuously formed, not less than a predetermined frequency of occurrence in a direction perpendicular to the convey direction of said web.

11. An apparatus according to claim 8, wherein said paster portion recognizing means comprises first detecting means for detecting that lateral pixel lines of said web which contain the defective pixels continue within a predetermined line count, and second detecting means for detecting that the number of longitudinal pixel lines containing the defective pixels is not less than a predetermined count in an area of the lateral pixel lines in which the defective pixels are continuously formed.

12. An apparatus according to claim 11, wherein said second detecting means comprises first means for logically ORing the defective pixels every longitudinal pixel line and second means for detecting that a sum of defective pixels of the logically ORed lateral pixel lines as a logical OR result is not less than a predetermined value.

13. An apparatus according to claim 8, further comprising rejecting means for eliminating, as printing defects, predetermined downstream and upstream areas with respect to said recognized paster portion as a boundary on the basis of an output from said paster portion recognizing means.

14. An apparatus according to claim 8, further comprising display means for displaying a position of said recognized paster portion and performing an alarm display of generation of said paster portion.

* * * * *